(12) United States Patent
Siegel et al.

(10) Patent No.: US 10,933,039 B2
(45) Date of Patent: Mar. 2, 2021

(54) COOLANT MIXTURES

(71) Applicant: Symrise AG, Holxminden (DE)

(72) Inventors: Sven Siegel, Höxter (DE); Arnold Machinek, Holzminden (DE); Bernd Hölscher, Halle (DE)

(73) Assignee: SYMRISE AG, Holxminden (DE)

( * ) Notice: Subject to any disclaimer, the term of this patent is extended or adjusted under 35 U.S.C. 154(b) by 0 days.

(21) Appl. No.: 16/099,082

(22) PCT Filed: May 5, 2016

(86) PCT No.: PCT/EP2016/060127
§ 371 (c)(1),
(2) Date: Nov. 5, 2018

(87) PCT Pub. No.: WO2017/190789
PCT Pub. Date: Nov. 9, 2017

(65) Prior Publication Data
US 2020/0179315 A1 Jun. 11, 2020

(51) Int. Cl.
A61K 31/19 (2006.01)
A61K 8/35 (2006.01)
A61K 8/36 (2006.01)
A61K 9/00 (2006.01)
A61K 9/68 (2006.01)
A61K 31/11 (2006.01)
A61Q 11/00 (2006.01)

(52) U.S. Cl.
CPC ............... A61K 31/19 (2013.01); A61K 8/35 (2013.01); A61K 8/36 (2013.01); A61K 9/0056 (2013.01); A61K 9/0058 (2013.01); A61K 31/11 (2013.01); A61Q 11/00 (2013.01)

(58) Field of Classification Search
None
See application file for complete search history.

(56) References Cited

U.S. PATENT DOCUMENTS

2011/0318459 A1 12/2011 Eapen

FOREIGN PATENT DOCUMENTS

| CN | 101156572 | 4/2008 |
| EP | 1050574 | 11/2000 |
| WO | 2013171018 | 11/2013 |

OTHER PUBLICATIONS

International Search Report and Written Opinion for PCT Application PCT/EP2016/060127 dated Oct. 17, 2016, pp. 1-13.
Lawrence B., "Some new trace constituents in the oil of Mentha Piperita L", Anais Da Academia Brasileira De Ciencias, vol. 44, pp. 191-197 (1972).
Samant S., et al, "Diversity, distribution and indigenous uses of essential oil-yielding medicinal plants of the indian himalayan region", Journal of Medicinal and Aromatic Plant Sciences, vol. 22, pp. 671-684 (2000).

*Primary Examiner* — Brian J Davis
(74) *Attorney, Agent, or Firm* — Michael P. Byrne; Wolter Van Dyke Davis, PLLC

(57) ABSTRACT

The invention relates to coolant mixtures containing: (a) at least one compound of formula (I), (b) at least one compound of formula (II) in which $R^1$ stands for hydrogen or a methyl group, $R^2$ stands for a methyl, ethyl or propyl group and n stands for 0, 1, or 2, and if applicable (c) an additional component.

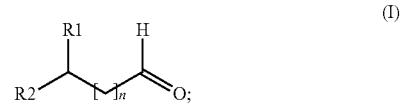

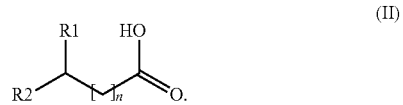

13 Claims, No Drawings

COOLANT MIXTURES

CROSS-REFERENCE TO RELATED APPLICATION

This application is a national stage entry of and claims priority to PCT/EP2016/060127, filed May 5, 2016, which is hereby incorporated by reference in its entirety.

FIELD OF THE INVENTION

The invention is in the field of oral preparations and relates to coolant mixtures with improved product properties and also to oral preparations comprising these substances.

BACKGROUND OF THE INVENTION

The term coolant is understood to mean chemical compounds which leave a cooling sensory impression on contact with skin or mucosa. Such substances are used in numerous cosmetic products, but the original and most important field of application is foodstuffs or more generally speaking, oral preparations. These also include mouth and dental care compositions and also certain pharmaceutical preparations, particularly those which are used for alleviating colds. The object of the coolant is to produce a refreshing but also soothing and sometimes even analgesic taste impression on the mucous membranes. In some cases, coolants also act as decongestant.

The most well-known coolant and still very important today is menthol, a monocyclic terpene alcohol, the essential constituent of which is mint oil. Since the 60s of the last century, coolants have been enriched in more ways by a multiplicity of novel compounds with different product properties such that a variety of alternatives can be called upon nowadays in product development. In the range of oral preparations, however, an unpleasant problem always makes itself felt which does not play any role in cosmetic applications: coolants often have unpleasant flavors, which—if they arise in the foreground—exclude use in the range of products which come into contact with mucosa. Such products are typically used in different combinations and various gradations with attributes such as "pungent", "stinging", "metallic", "bitter" or "sharp". Some of these substances have been shown to be in the position to bring the oral flora out of equilibrium.

Therefore, there still exists considerable interest in coolants, especially an intelligent mixing of known representatives, which possess an improved taste and performance profile.

The object of the present therefore consisted specifically of improving the cooling effect of known coolants by selective mixing such that at the same time

- a relatively high cooling effect is achieved on oral administration,
- the cooling effect sets in rapidly,
- the oral flora is maintained in a healthy balance,
- a bitter taste impression, particularly in combination with menthol, is prevented or significantly reduced,
- the unpleasant taste impression, which various coolants possess, is mitigated, and
- a soothing effect is imparted to the throat and voice.

DESCRIPTION OF THE INVENTION

The invention firstly provides coolant mixtures comprising
(a) at least one compound of the formula (I)

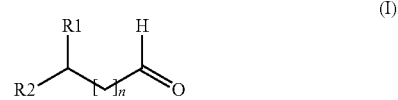

(b) at least one compound of the formula (II)

wherein $R^1$ is in each case hydrogen or a methyl group, $R^2$ is in each case a methyl, ethyl or propyl group and n is 1 or 2, and also optionally
(c) a further coolant.

Surprisingly, it has been found that preparations comprising at least one coolant known per se from groups (a) and (b) fully achieve the complex object described at the outset. Whereas the substances of the formulae (I) and (II) taken individually often trigger an unpleasant pungent or even stinging taste, mixtures thereof are distinctly milder and may even cover up the bitter taste of menthol. On the contrary, they even have a soothing effect on throat and voice. A further advantage consists in that the cooling effect of the mixtures is perceived as distinctly stronger and has a more rapid onset. Finally, the mixtures do not impair the composition of the oral flora in a disadvantageous manner. The effects outlined become evident particularly significantly when component (a) is used in significant excess by weight to component (b).

Coolants of Groups A and B

Examples of substances which form component (a) are isobutyraldehyde (2220), isovaleraldehyde (2692) and mixtures thereof.

Examples of substances which form component (b) are isobutyric acid (2222), isovaleric acid (2694) and mixtures thereof.

The substances specified represent known coolants which physiologically tolerable and are approved for oral administration. The numbers stated above in parentheses refer to the corresponding GRAS FEMA registration of these substances.

In a preferred embodiment, the mixtures according to the invention comprise at least one of the following mixtures of components (a) and (b):

(i) isobutyraldehyde and isobutyric acid;
(ii) isovaleraldehyde and isovaleric acid;
(iii) isobutyraldehyde and isovaleric acid;
(iv) isovaleraldehyde and isobutyric acid;
(v) isobutyraldehyde, isobutyric acid, isovaleraldehyde and isovaleric acid.

The mixtures may contain components (a) and (b) in a weight ratio from 9999.9:1 to 9:1. Preferred weight specifications are from 999:1 to 99:1 and especially 90:1 to 19:1.

Further Coolants

As optional constituents, the mixtures according to the invention may contain further coolants in which preference is given to menthol and/or menthol compounds.

Coolants which may be used in the context of the invention and which form group (c)—in addition to the basic component menthol itself—are selected for example from the group comprising menthol methyl ether, menthone glyceryl acetal (FEMA GRAS[1] 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl N-ethyloxamate, monomethyl succinate (FEMA GRAS 3810), monomenthyl glutamate (FEMA GRAS 4006), menthoxy-1,2-propanediol (FEMA GRAS 3784), menthoxy-2-methyl-1,2-propanediol (FEMA GRAS 3849) and also the menthane carboxylic esters and amides WS-3, WS-4, WS-5, WS-12, WS-14 and WS-30 and mixtures thereof.

[1] FEMA stands for "Flavor and Extracts Manufacturers Association" and GRAS is defined as "Generally Regarded As Safe". A FEMA GRAS designation signifies that the substance thus characterized is tested according to a standard method and is deemed to be of no toxicological concern.

A first important representative of the substances which form component (b) is monomenthyl succinate (FEMA GRAS 3810), which has been patented as a substance since 1963 by Brown & Williamson Tobacco Corp. (U.S. Pat. No. 3,111,127) and as a coolant is subject to the patent rights U.S. Pat. Nos. 5,725,865 and 5,843,466 (V. Mane Fils). Both the succinate and the analogous monomenthyl glutarate (FEMA GRAS 4006) are important representatives of monomenthyl esters based on di- and polycarboxylic acids:

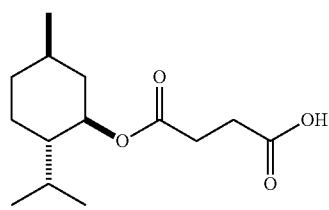

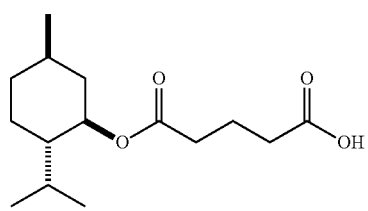

Examples of uses of these substances are found, for example, in publications WO 2003 043431 (Unilever) or EP 1332772 A1 (IFF).

The next important group in the context of the invention of preferred menthol compounds includes carbonate esters of menthol and polyols, such as, for example, glycols, glycerol or carbohydrates, such as menthol ethylene glycol carbonate (FEMA GRAS 3805=Frescolat® MGC), menthol propylene glycol carbonate (FEMA GRAS 3784=Frescolat® MPC), menthol 2-methyl-1,2-propanediol carbonate (FEMA GRAS 3849) or the corresponding sugar derivatives:

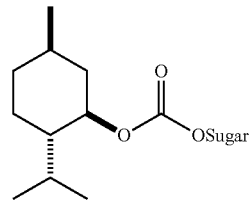

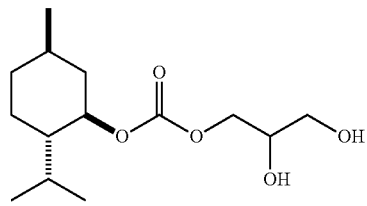

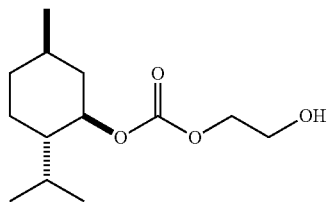

Menthol ethylene glycol carbonate

The use of such substances as coolants for cigarettes is for example the subject matter of publication U.S. Pat. No. 3,419,543 (Mold et al.) from the year 1968; the application as physiological coolant is claimed in DE 4226043 A1 (H&R).

In the context of the invention, preference is given to the menthol compounds menthyl lactate (FEMA GRAS 3748=Frescolat® ML) and especially to menthone glyceryl acetal (FEMA GRAS 3807) and menthone glyceryl ketal (FEMA GRAS 3808), which is marketed under the name Frescolat® MGA.

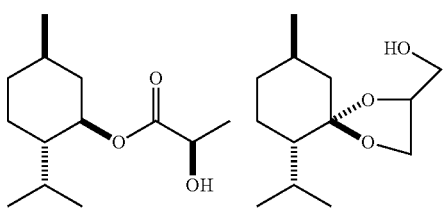

The former structure is obtained by esterification of lactic acid with menthol, the latter by acetalization of menthone with glycerol (cf. DE 2608226 A1, H&R). Included in this group of compounds is also 3-(1-menthoxy)-1,2-propanediol, which is also known as Cooling Agent 10 (FEMA GRAS 3784, cf. U.S. Pat. No. 6,328,982, TIC), and also 3-(1-menthoxy)-2-methyl-1,2-propane-dial (FEMA GRAS 3849), which has an additional methyl group.

Cooling Agent 10

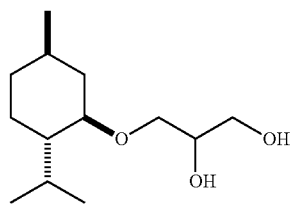

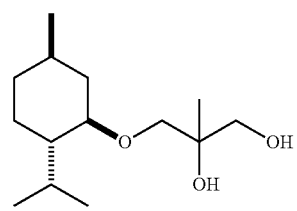

l-Menthoxy-2-methyl 1,2-propanediol 3-(1-Menthoxy)-1,2-propanediol is prepared, for example, starting from menthol according to the following scheme (cf. U.S. Pat. No. 4,459,425, Takagaso):

Alternative routes, in which in the first stage menthol is reacted with epichlorohydrin, is described in U.S. Pat. Nos. 6,407,293 and 6,515,188 (Takagaso). In the following, an overview of the preferred menthol compounds is given which are characterized by a CO bond:

3748

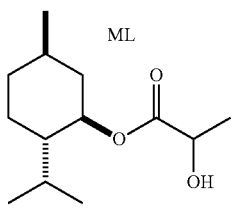
ML

3807

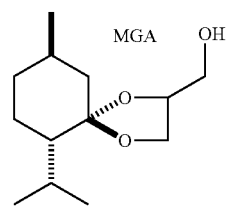
MGA

3784

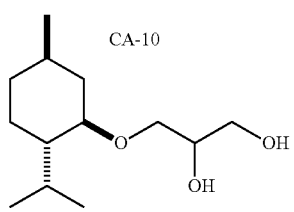
CA-10

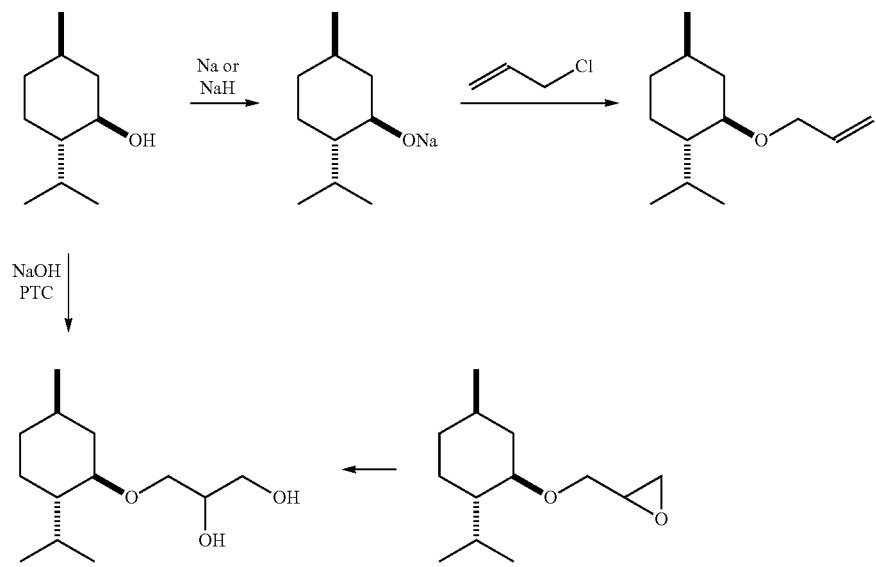

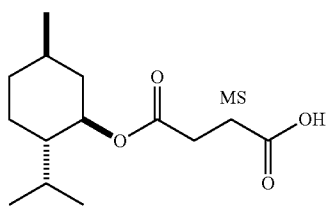

3810

MS

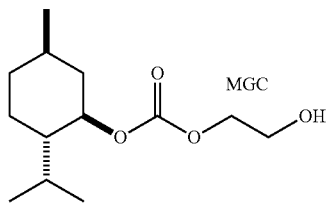

3805

MGC

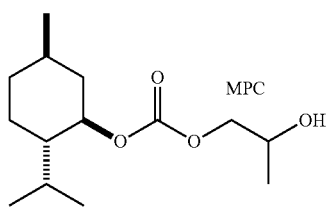

3806

MPC

Proven to be very particularly advantageous among these substances are menthone glyceryl acetal/ketal and menthyl lactate and also menthol ethylene glycol carbonate or menthol propylene glycol carbonate, which are distributed by the applicant under the names Frescolat® MGA, Frescolat® ML, Frescolat® MGC and Frescolat® MPC.

4006

MG

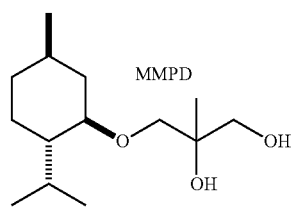

3849

MMPD

In the 70s of the last century, menthol compounds were developed for the first time having a C—C bond in the 3-position and from which a series of representatives may also be used in the context of the invention. These substances are generally referred to as WS types. The basic component is a menthol derivative in which the hydroxyl group is replaced by a carbonyl group (WS-1). All other WS types are derived from this structure, such as, for example, the species WS-3, WS-4, WS-5, WS-12, WS-14 and WS-30, that are also preferred in the context of this invention The two schemes which follow show the synthetic routes:

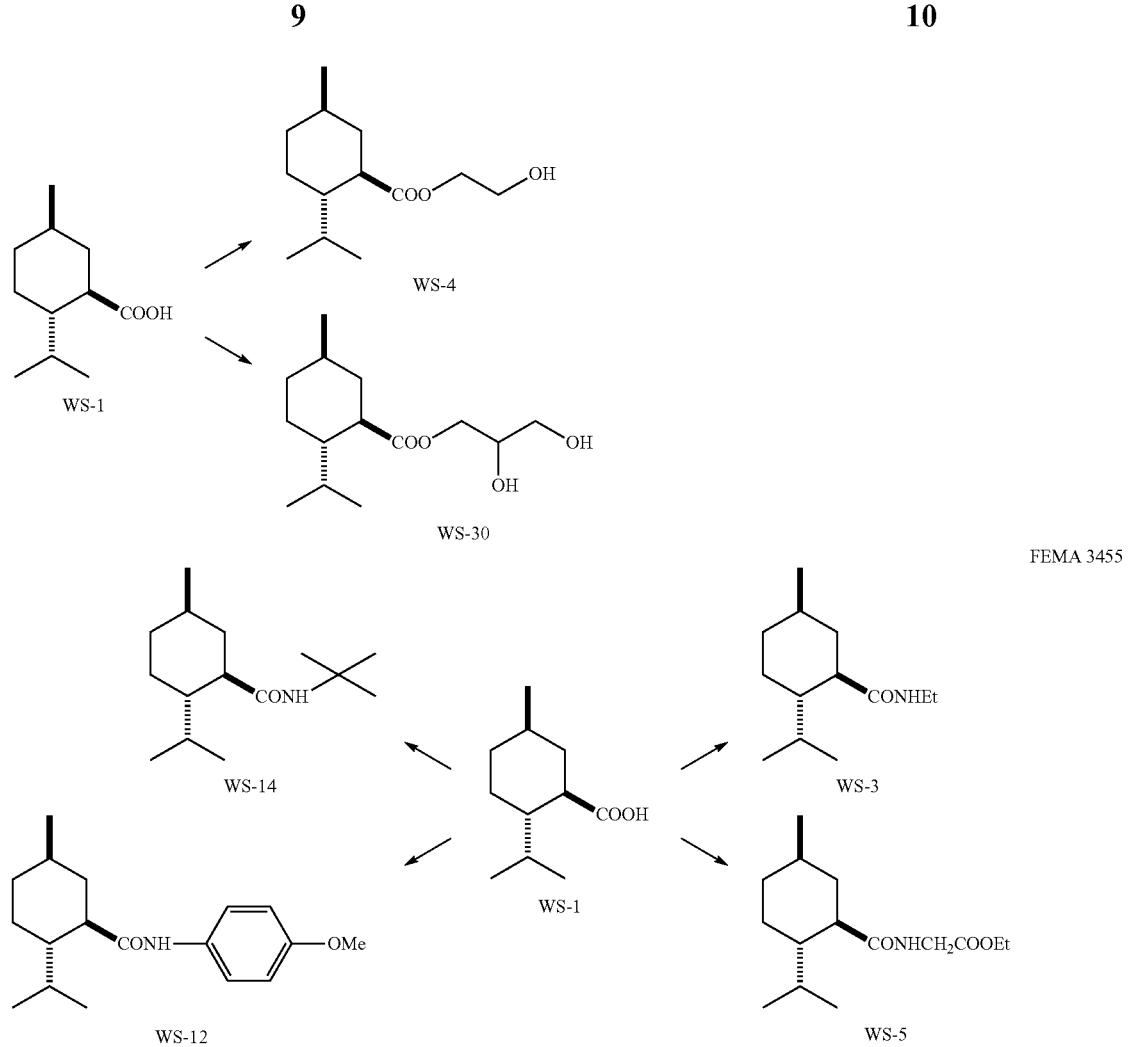

The esters derived from WS-1 are described, for example, in U.S. Pat. No. 4,157,384, the corresponding N-substituted amides in J. Soc. Cosmet. Chem. pp. 185-200 (1978).

In a further preferred embodiment of the invention, the mixtures comprise the components in the following amounts:
 (a) about 90 to about 99% by weight and especially about 95 to about 98% by weight substances of the formula (I),
 (b) about 1 to about 10% by weight and especially about 5 to about 8% by weight substances of the formula (II), and
 (c) 0 to about 90% by weight and especially about 1 to about 5% by weight further coolants with the proviso that the components add up to 100% by weight.

Particular preference is given to mixtures comprising the components in the following amounts:
 (a) 0.0001 to 10% by weight substances of the formula (I)
 (b) 0.0001 to 10% by weight substances of the formula (II)
 (c1) 0 to 7% by weight and especially 0.1 to 5% by weight menthol and
 (c2) 0 to 20% by weight, especially 0.5 to 10% by weight menthyl acetate with the proviso that the components add up to 100% by weight. With this restriction, it is clarified that all mixing ratios which do not add up to 100% by weight are excluded and a person skilled in the art can select any mixing ratios within the specifications which meet the teaching relating to the above without having to involve an inventive step in this regard. Otherwise, reference is made to the working examples.

Commercial Applicability

The present invention furthermore provides preparations for oral administration comprising the coolant mixtures described above. These preparations can take the form of food-stuffs, pharmaceutical preparations or mouth and dental care compositions, wherein the transition between these groups is fluid. A chewy candy can for example also be used as confectionery and as cold remedy, a chewing gum can likewise serve as refreshment or even for medicinal dental care.

Oral Preparations

Typical examples of foodstuffs comprising the preparations according to the invention are hard candies, chewy candies or chewing gums.

Typical examples of pharmaceutical preparations comprising the preparations according to the invention are cold remedies such as syrups, sprays or candies.

Typical examples of pharmaceutical preparations comprising the preparations according to the invention are toothpastes, mouthwashes or medicinal chewing gums.

The oral preparations mentioned may comprise the coolant mixtures in amounts from about 0.5 to about 5% by weight and especially about 1 to about 2.5% by weight—based on the finished preparation. In the following, auxiliaries and additives are described which may also be present in the oral preparations.

Foodstuffs

Foodstuffs which may contain the coolant mixtures according to the invention are generally hard candies or chewy candies and boiled sweets. The most important additive for these products are sweeteners, among which especially are those which are not sugar-based. In addition, aromas and food dyes especially should be mentioned.

Sweeteners

Suitable as sweeteners or sweet-tasting additives are firstly carbohydrates and especially sugar, such as for example sucrose, trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, or maltodextrin. Also suitable are plant preparations comprising these substances, for example based on sugar beet (*Beta vulgaris* ssp., sugar fractions, sugar syrup, molasses), sugar cane (*Saccharum officinarum* ssp., molasses, sugar cane syrup), maple syrup (*Acer* ssp.) or agaves (thick agave juice).

Also suitable are synthetic, i.e. in general enzymatically produced starch or sugar hydrolysates (invert sugar, fructose syrup);
- fruit concentrates (e.g. based on apples or pears);
- sugar alcohols (e.g. erythritol, threitol, arabitol, ribotol, xylitol, sorbitol, mannitol, dulcitol, lactitol);
- proteins (e.g. miraculin, monellin, thaumatin, curculin, brazzein);
- sweeteners (e.g. magap, sodium cyclamate, acesulfam K, neohesperidin dihydrochalcone, saccharin sodium salt, aspartame, superaspartame, neotame, alitame, sucralose, stevioside, rebaudioside, lugduname, carrelame, sucrononate, sucrooctate, monatin, phenylodulcin);
- Sweet-tasting amino acids (e.g. glycine, D-leucine, D-threonine, D-asparagine, D-phenylalanine, D-tryptophan, L-proline);
- Further sweet-tasting low molecular weight substances such as e.g. hernandulcin, dihydrochalcone glycosides, glycyrrhizin, glycerrhetic acid, derivatives and salts thereof, extracts of liquorice (*Glycyrrhizza glabra* ssp.), *Lippia dulcis* extracts, *Momordica* ssp. extracts or
- single substances such as e.g. *Momordica grosvenori* [Luo Han Guo] and mogrosides obtained therefrom, *Hydrangea dulcis* or *Stevia* ssp. (e.g. *Stevia rebaudiana*) extracts.

Flavorings

In the oral preparations, the invention also allows in particular the use of flavorings having ester, aldehyde or lactone structures which are degraded particularly rapidly in the presence of titanium dioxide or under the influence of light. The invention also therefore ensures an improved stability, especially storage stability, of the flavorings.

The oral preparations according to the invention may also contain one or more flavorings. Typical examples include: acetophenone, allyl caproate, alpha-ionone, beta-ionone, anisaldehyde, anisyl acetate, anisyl formate, benzaldehyde, benzothiazole, benzyl acetate, benzyl alcohol, benzyl benzoate, beta-ionone, butyl butyrate, butyl caproate, butylidenephthalide, carvone, camphene, caryophyllene, cineol, cinnamyl acetate, citral, citronellol, citronellal, citronellyl acetate, cyclohexyl acetate, cymol, damascone, decalactone, dihydrocoumarin, dimethyl anthranilate, dodecalactone, ethoxyethyl acetate, ethylbutyric acid, ethyl butyrate, ethyl caprinate, ethyl caproate, ethyl crotonate, ethyl furaneol, ethyl guaiacol, ethyl isobutyrate, ethyl isovalerate, ethyl lactate, ethyl methylbutyrate, ethyl propionate, eucalyptol, eugenol, ethyl heptylate, 4-(p-hydroxyphenyl)-2-butanone, gamma-decalactone, geraniol, geranyl acetate, grapefruit aldehyde, methyl dihydrojasmonate (e.g. Hedion®), heliotropine, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl caproate, trans-2-hexenyl caproate, cis-3-hexenyl formate, cis-2-hexyl acetate, cis-3-hexyl acetate, trans-2-hexyl acetate, cis-3-hexyl formate, para-hydroxybenzylacetone, isoamylalcohol, isoamyl isovalerate, isobutyl butyrate, isobutyralde-hyde, isoeugenol methyl ether, isopropylmethylthiazole, lauric acid, levulinic acid, linalool, linalool oxide, linalyl acetate, menthol, menthofuran, methyl anthranilate, methylbutanol, methylbutyric acid, 2-methylbutyl acetate, methyl caproate, methyl cinnamate, 5-methyl-furfural, 3,2,2-methylcyclopentenolone, 6,5,2-methylheptenone, methyl dihydrojasmonate, methyl jasmonate, 2-methyl methylbutyrate, 2-methyl-2-pentenolic acid, methyl thiobutyrate, 3,1-methylthiohexanol, 3-methylthiohexyl acetate, nerol, neryl acetate, trans,trans-2,4-nonadienal, 2,4-nonadienol, 2,6-nonadienol, 2,4-nonadienol, nootkatone, delta octalactone, gamma octalactone, 2-octanol, 3-octanol, 1,3-octenol, 1-octyl acetate, 3-octyl acetate, palmitic acid, paraldehyde, phellandrene, pentanedione, phenylethyl acetate, phenylethyl alcohol, phenylethyl alcohol, phenylethyl isovalerate, piperonal, propionaldehyde, propyl butyrate, pulegone, pulegol, sinensal, sulfurol, terpinene, terpineol, terpinols, 8,3-thiomenthanone, 4,4,2-thiomethylpentanone, thymol, delta-undecalactone, gamma-undecalactone, valencene, valeric acid, vanillin, acetoin, ethylvanillin, ethylvanillin isobutyrate (=3-ethoxy-4-isobutyryloxybenzaldehyde), 2,5-dimethyl-4-hydroxy-3(2H)-furanone and derivatives thereof (here preferably homofuraneol) (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (here preferably ethyl maltol), coumarin and coumarin derivatives, gamma-lactones (here preferably gamma-undecalactone, gamma-nonalactone, gamma-decalactone), delta-lactones (here preferably 4-methyl deltadecalactone, massoia lactone, deltadecalactone, tuberolactone), methyl sorbate, divanillin, 4-hydroxy-2(or 5)-ethyl-5(or 2)-methyl-3(2H)-furanone, 2-hydroxy-3-methyl-2-cyclopentenone, 3-hydroxy-4,5-dimethyl-2(5H)-furanone, acetic acid isoamyl ester, butyric acid ethyl ester, butyric acid n-butyl ester, butyric acid isoamyl ester, 3-methyl-butyric acid ethyl ester, n-hexanoic acid ethyl ester, n-hexanoic acid allyl ester, n-hexanoic acid-n-butyl ester, n-octanoic acid ethyl ester, ethyl 3-methyl-3-phenylglycidate, ethyl 2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methylthio)furan, 2-methyl-3-furanthiol, bis(2-methyl-3-furyl) disulfide, furfuryl mercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2(5H)-furanone, cinnamaldehyde, cinnamyl alcohol, methyl salicylate, isopulegol and (not explicitly stated here) stereoisomers, enantiomers, positional isomers, diastereomers, cis/trans isomers or epimers of these substances.

Flavor Enhancers

The oral preparations—in addition to the aroma mixtures—may also contain additional flavorings for enhancing a salty, optionally slightly acidic and/or umami taste impression. The products according to the invention and aroma mixtures are therefore used in combination with at least one further substance suitable for enhancing a pleasant taste impression (salty, umami, optionally slightly acidic). Preference is given to salty-tasting compounds and salt-enhancing compounds. Preferred compounds are disclosed in WO 2007/045566. Further preferred are umami compounds such as are described in WO 2008/046895 and EP 1 989 944.

Furthermore, preferred products in accordance with the invention may also include flavorings for masking bitter and/or astringent taste impressions (flavor correctants). The (further) flavor correctants are selected, for example, from the following list: nucleotides (e.g. adenosine-5'-monophosphate, cytidine-5'-monophosphate) or pharmaceutically acceptable salts thereof, lactisole, sodium salts (e.g. sodium chloride, sodium lactate, sodium citrate, sodium acetate, sodium gluconate), further hydroxyflavanones (e.g. eriodictyol, homoeriodictyol or sodium salts thereof), especially in accordance with US 2002/0188019, hydroxybenzoic acid amides according to DE 10 2004 041 496 (e.g. 2,4-dihydroxybenzoic acid vanillylamide, 2,4-dihydroxybenzoic acid N-(4-hydroxy-3-methoxybenzyl)amide, 2,4,6-trihydroxybenzoic acid N-(4-hydroxy-3-methoxybenzyl)amide, 2-hydroxybenzoic acid N-4-(hydroxy-3-methoxybenzyl)amide, 4-hydroxybenzoic acid N-(4-hydroxy-3-methoxybenzyl)amide, 2,4-dihydroxybenzoic acid N-(4-hydroxy-3-methoxybenzyl)amide monosodium salt, 2,4-dihydroxybenzoic acid N-2-(4-hydroxy-3-methoxyphenyl)ethylamide, 2,4-dihydroxybenzoic acid N-(4-hydroxy-3-ethoxybenzyl)amide, 2,4-dihydroxybenzoic acid N-(3,4-dihydroxybenzyl)amide and 2-hydroxy-5-methoxy-N-[2-(4-hydroxy-3-methoxyphenyl)ethyl]amide (aduncamide), 4-hydroxybenzoic acid vanillylamide), bitter-masking hydroxydeoxybenzoins e.g. in accordance with WO 2006/106023 (e.g. 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone, 1-(2-hydroxy-4-methoxyphenyl)-2-(4-hydroxy-3-methoxyphenyl)ethanone), amino acids (e.g. gamma-aminobutyric acid according to WO 2005/096841 for reducing or masking an unpleasant taste impression such as bitterness), malic acid glycosides according to WO 2006/003107, salty-tasting mixtures according to PCT/EP 2006/067120 diacetyltrimers according to WO 2006/058893, mixtures of whey proteins with lecithins and/or bitter-masking substances such as gingerdione according to WO 2007/003527.

Preferred flavorings are those which cause a sweet odor impression, wherein the further flavoring(s) which cause a sweet odor impression are preferably selected from the group consisting of:

Vanillin, ethylvanillin, ethylvanillin isobutyrate (=3-ethoxy-4-isobutyryloxybenzaldehyde), furaneol (2,5-dimethyl-4-hydroxy-3(2H)-furanone) and derivatives (e.g. homofuraneol, 2-ethyl-4-hydroxy-5-methyl-3(2H)-furanone), homofuronol (2-ethyl-5-methyl-4-hydroxy-3(2H)-furanone and 5-ethyl-2-methyl-4-hydroxy-3(2H)-furanone), maltol and derivatives (e.g. ethylmaltol), coumarin and derivatives, gamma-lactones (e.g. gamma-undecalactone, gamma-nonalactone), delta-lactones (e.g. 4-methyldeltalactone, massoia lactone, deltadecalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, fruit esters and fruit lactones (e.g. n-butyl acetate, isomayl acetate, ethyl propionate, ethyl butyrate, n-butyl butyrate, isoamyl butyrate, ethyl 3-methylbutyrate, ethyl n-hexanoate, allyl n-hexanoate, n-butyl n-hexanoate, ethyl n-octanoate, ethyl 3-methyl-3-phenylglycidate, ethyl 2-trans-4-cis-decadienoate), 4-(p-hydroxyphenyl)-2-butanone, 1,1-dimethoxy-2,2,5-trimethyl-4-hexane, 2,6-dimethyl-5-hepten-1-al, 4-hydroxycinnamic acid, 4-methoxy-3-hydroxycinnamic acid, 3-methoxy-4-hydroxycinnamic acid, 2-hydroxycinnamic acid, 2,4-dihydroxybenzoic acid, 3-hydroxybenzoic acid, 3,4-dihydroxybenzoic acid, vanillic acid, homovanillic acid, vanillylmandelic acid and phenylacetaldehyde.

Active Ingredients for Masking Unpleasant Taste Impressions

Furthermore, the oral preparations may also contain further substances which also serve for masking bitter and/or astringent taste impressions. These further flavor correctants are selected, for example, from the following list: nucleotides (e.g. adenosine-5'-monophosphate, cytidine-5'-monophosphate) or physiologically tolerable salts thereof, lactisoles, sodium salts (e.g. sodium chloride, sodium lactate, sodium citrate, sodium acetate, sodium gluconate), hydroxyflavanones, preferred here eriodictyol, sterubin (eriodictyol 7-methyl ether), homoeriodictyol, and sodium, potassium, calcium, magnesium or zinc salts thereof (especially those described in EP 1258200 A2, which with respect to the corresponding compounds disclosed therein is by reference a constituent of this application), hydroxybenzoic acid amides, preferably here 2,4-dihydroxybenzoic acid vanillylamide, 2,4-dihydroxybenzoic acid N-(4-hydroxy-3-methoxybenzyl)amide, 2,4,6-trihydroxybenzoic acid N-(4-hydroxy-3-methoxybenzyl)amide, 2-hydroxybenzoic acid N-4-(hydroxy-3-methoxybenzyl)amide, 4-hydroxybenzoic acid N-(4-hydroxy-3-methoxybenzyl)amide, 2,4-dihydroxybenzoic acid N-(4-hydroxy-3-methoxybenzyl)amide monosodium salt, 2,4-dihydroxybenzoic acid N-2-(4-hydroxy-3-methoxyphenyl)ethylamide, 2,4-dihydroxybenzoic acid N-(4-hydroxy-3-ethoxybenzyl)amide, 2,4-dihydroxybenzoic acid N-(3,4-dihydroxybenzyl)amide and 2-hydroxy-5-methoxy-N-[2-(4-hydroxy-3-methoxyphenyl)ethyl]amide; 4-hydroxybenzoic acid vanillylamides (especially those described in WO 2006/024587, which with respect to the corresponding compounds disclosed therein is by reference a constituent of this application); hydroxydeoxybenzoins, here preferably 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone and 1-(2-hydroxy-4-methoxyphenyl)-2-(4-hydroxy-3-methoxyphenyl)ethanone) (especially those described in WO 2006/106023, which with respect to the corresponding compounds disclosed therein is by reference a constituent of this application); hydroxyphenylalkanediones, such as for example gingerdione-[2], gingerdione-[3], gingerdione-[4], dehydrogingerdione-[2], dehydrogingerdione-[3], dehydrogingerdione-[4]) (especially those as described in WO 2007/003527, which with respect to the corresponding compounds disclosed therein is by reference a constituent of this application); diacetyl trimers (especially those described in WO 2006/058893, which with respect to the corresponding compounds disclosed therein is by reference a constituent of this application); gamma-aminobutyric acids (especially those described in WO 2005/096841, which with respect to the corresponding compounds disclosed therein is by reference a constituent of this application); divanillins (especially those described in WO 2004/078302, which with respect to the corresponding compounds disclosed therein is by reference a constituent of this application) and 4-hydroxydihydrochalcones (preferably as described in US 2008/0227867 A1, which with respect to the corresponding compounds disclosed therein is by reference a constituent of this application), particularly here phloretin and davidigenin, amino acids or mixtures of whey proteins with lecithins, hesperetin as disclosed in WO 2007/014879, which with respect to these compounds is by reference a constituent of this application, 4-hydroxydihydrochalcones such as disclosed in WO 2007/107596, which with respect to these compounds is by reference a constituent of this application, or propenyl phenylglycosides (chavicol glycosides) such as described in EP 1955601 A1, which with respect to these compounds is by reference a constituent of this application, or extracts of *Rubus suavissimus*, extracts of *Hydrangea macrophylla* such as described in EP 2298084 A1, pellitorin and derived aroma compositions such as described in EP 2008530 A1, umami compounds such as described in WO 2008/046895 A1 and EP 1989944 A1, umami compounds as descibed in EP 2064959 A1 and EP 2135516 A1, vanillyl lignans, enterodiol, and also N-decadienoylamino acids and mixtures thereof.

Food Colorings

Food colorings or colorings for short are food additives for coloring foods. Colorings are subdivided into the groups of natural dyes and synthetic dyes. The nature-identical colorings are also of synthetic origin. The nature-identical colorings are replicates of coloring substances that occur in nature. Suitable colorings for use in the present composition are selected from: curcumin, E 100 riboflavin, lactoflavin, vitamin B2, E 101 tartrazine, E 102 quinoline yellow, E 104 yellow-orange S, yellow-orange RGL, E 110 cochineal, carminic acid, true carmine, E 120 azorubine, carmoisine, E 122 amaranth, E 123 cochineal red A, Ponceau 4 R, Victoria scarlet 4 R, E 124 erythrosine, E 127 Allura red AC, E 129 Patent blue V, E 131 indigotin, indigo carmine, E 132 Brilliant Blue FCF, Patent Blue AE, Amido Blue AE, E 133 chlorophylls, chlorophyllins, E 140 copper complexes of chlorophylls, copper-chlorophyllin complex, E 141 Brilliant Acid Green, Green S, E 142 caramel colour, E 150 a sulphite lye caramel colour, E 150 b ammonia caramel colour, E 150 c ammonium sulphite caramel colour, E 150 d Brilliant Black FCF, Brilliant Black PN, Black PN, E 151 vegetable charcoal, E 153 Brown FK, E 154 Brown HT, E 155 carotene, E 160 a annatto, bixin, norbixin, E 160 b capsanthin, capsorubin, E 160 clycopene, E 160 d beta-apo-8'-carotenal, apocarotenal, beta-apocarotenal, E 160 e beta-apo-8'-carotenoic acid ethyl ester (C30), apocarotene esters, beta-carotenoic esters, E 160 f lutein, xanthophyll, E 161 b canthaxanthin, E 161 g betanin, beet red, E 162 anthocyans, E 163 calcium carbonate, E 170 titanium dioxide, E 171 iron oxides, iron hydroxides, E 172 aluminium, E 173 silver, E 174 gold, E 175 lithol rubine BK, rubine pigment BK, E 180.

Chewing Gums

The preferred oral preparations may also particularly be in the form of chewing gums. These products typically comprise a water-insoluble and a water-soluble component.

The water-insoluble base, also known as "gum base", usually comprises natural or synthetic elastomers, resins, fats and oils, plasticizers, fillers, dyes and also optionally waxes. The fraction of base of the total composition is usually 5 to 95% by weight, preferably 10 to 50% by weight and in particular 20 to 35% by weight. In a typical embodiment of the invention, the base is 20 to 60% by weight composed of synthetic elastomers, 0 to 30% by weight natural elastomers, 5 to 55% by weight plasticizers, 4 to 35% by weight fillers and in subsidiary amounts additives such as dyes, antioxidants and the like, with the proviso that they are water-soluble, at all events in small amounts.

Suitable synthetic elastomers are, for example, polyisobutylenes having average molecular weights (according to GPC) of 10 000 to 100 000, and preferably 50 000 to 80 000, isobutylene-isoprene-copolymers ("butyl elastomers"), styrene-butadiene-copolymers (styrene:butadiene ratio e.g. 1:3 to 3:1), polyvinylacetates having average molecular weights (according to GPC) of 2000 to 90 000, and preferably 10 000 to 65 000, polyisoprenes, polyethylene, vinyl acetate-vinyl laurate copolymers and mixtures thereof. Examples of suitable natural elastomers are rubbers, for instance smoked or liquid latex or Guayule and also natural rubbers such as jelutong, lechi caspi, perillo, sorva, massaranduba balata, massaranduba chocolate, nispero, rosindinba, chicle, gutta hang kang, and also mixtures thereof. The selection of synthetic and natural elastomers and mixing ratios thereof is directed substantially according to whether bubbles are to be generated ("bubble gums") or not with the chewing gums. Preferably, elastomer mixtures are used which contain jelutong, chicle, sorva and massaranduba.

In most cases, the elastomers prove in processing to be too hard or insufficiently manageable, and so it has proved advantageous to use conjointly specific plasticizers which of course must in particular also meet all the requirements to be permitted as food additives. In this respect, chiefly esters of resin acids come into consideration, for example esters of low aliphatic alcohols or polyols with completely or partially hardened, monomeric or oligomeric resin acids. In particular for this purpose, the methyl, glycerol or pentarerythrityl esters and also mixtures thereof are used. Alternatively, terpene resins also come into consideration which can be derived from alpha-pinene, beta-pinene, delta-limonene or mixtures thereof.

As fillers or texturizing agents come magnesium or calcium carbonate, ground pumice stone, silicates, especially magnesium or aluminium silicates, clays, aluminas. Talcum, titanium dioxide, mono, di and tricalciumphosphate and also cellulose polymers.

Suitable emulsifiers are tallow, hardened tallow, hardened or partially hardened vegetable oils, cocoa butter, partial glycerides, lecithin, triacetin and saturated or unsaturated fatty acids having 6 to 22, and preferably 12 to 18, carbon atoms, and also mixtures thereof.

As dyes and whitening agents, for example the FD and C types, plant and fruit extracts and also titanium dioxide permitted for colouring foods come into consideration.

The base compositions can contain waxes or be wax free; examples of wax-free compositions may be found, inter alia, in the patent document U.S. Pat. No. 5,286,500, the content of which is hereby explicitly incorporated by reference.

In addition to the water-insoluble gum base, chewing gum preparations regularly contain a water-soluble fraction which are formed, for example, by softeners, sweeteners, fillers, taste substances, taste enhancers, emulsifiers, dyes, acidulants, antioxidants and the like, here with the proviso that the components have an at least adequate water solubility. Depending on the water solubility of the specific representatives, therefore, individual components can either belong to the water-insoluble phase or else the water-soluble phase. However, it is also possible to use combinations, for example of a water-soluble emulsifier and a water-insoluble emulsifier, wherein the individual representatives are then located in different phases. Usually, the water-insoluble fraction makes up 5 to 95% by weight, and preferably 20 to 80% by weight, of the preparation.

Water-soluble softeners or plasticizing agents are added to the chewing gum compositions in order to improve the chewability and the chewing feel and are present in the mixtures typically in amounts of 0.5 to 15% by weight. Typical examples are glycerol, lecithin and also aqueous solutions of sorbitol, hardened starch hydrolysates or corn syrup.

As sweeteners, both sugar-containing and sugar-free compounds come into consideration which are used in amounts of 5 to 95% by weight, preferably 20 to 80% by weight, and in particular 30 to 60% by weight, based on the chewing gum composition. Typical saccharide sweeteners are sucrose, dextrose, maltose, dextrin, dried invert sugar, fructose, levulose, galactose, corn syrup, and also mixtures thereof. As sugar replacers, sorbitol, mannitol, xylitol, hardened starch hydrolysates, maltitol and mixtures thereof come into consideration. In addition, as additives, what are termed HIAS ("High Intensity Artificial Sweeteners") also come into consideration, such as, for example, sucralose, aspartame acesulfame salts, alitame, saccharin and saccharin salts, cyclamic acid and salts thereof, glycyrrhizins, dihydrochalcones, thaumatin, monellin and the like, alone or in mixtures. Particularly effective also are the hydrophobic HIAS, the subject matter of the international patent application WO 2002 091849 A1(Wrigleys) and also Stevia extracts and active constituents thereof, especially Ribeaudiosid A. The amount used of these substances depends primarily on their capacity and is typically in the range from 0.02 to 8% by weight.

In particular, for the production of low-calorie chewing gums, fillers such as, for example, polydextrose, raftilose, Rafitilin, fructooligosaccharides (NutraFlora), palatinose oligosaccharides, guar gum hydrolysates (Sun Fiber) and also dextrins are suitable.

The selection of further taste substances is virtually unlimited and is non-critical for the essence of the invention. Usually, the total fraction of all taste substances is 0.1 to 15% by weight, and preferably 0.2 to 5% by weight, based on the chewing gum composition. Suitable further taste substances are, for example, essential oils, synthetic flavourings and the like, such as, for instance, aniseed oil, star anise oil, cumin oil, eucalyptus oil, fennel oil, lemon oil, wintergreen oil, clove oil and the like, as are also used, for example, in oral and dental care compositions.

The chewing gums can contain further auxiliaries and additives which are suitable, for example, for tooth care, especially for combating plaque and gingivitis, such as, e.g., chlorhexidine, CPC or triclosan. In addition, pH regulators (e.g. buffers or urea), substances active against caries (e.g. phosphates or fluorides), biogenic active ingredients (antibodies, enzymes, caffeine, plant extracts) may be present, provided that these substances are permitted for foods, and do not interact with one another in an undesired manner.

Oral and Dental Care Compositions

Inventive oral consumable sweet-tasting products may serve particularly for cleaning and caring for mouth and teeth. Examples of these are said toothpastes, tooth gels, tooth powders, mouthwashes and the like. Toothpastes or tooth creams are generally taken to mean gel-type or pasty preparations of water, thickeners, moisture-retention agents, abrasive or cleaning bodies, surfactants, sweeteners, aroma substances, deodorizing active ingredients and also active ingredients against oral and dental diseases. All customary cleaning bodies, such as, e.g. chalk, dicalcium phosphate, insoluble sodium metaphosphate, aluminium silicates, calcium pyrophosphate, finely divided synthetic resins, silicas, aluminium oxide and aluminium oxide trihydrate can be used in the toothpastes according to the invention.

Preferably suitable cleaning bodies for the toothpastes according to the invention are, especially, finely divided xerogel silicas, hydrogel silicas, precipitated silicas, aluminium oxide trihydrate and finely divided alpha-aluminium oxide or mixtures of these cleaning bodies in amounts of 15 to 40% by weight of the toothpaste. As moisture-retention agents, principally low-molecular-weight polyethylene glycols, glycerol, sorbitol or mixtures of these products in amounts up to 50% by weight come into consideration. Among the known thickeners, the thickening, finely divided gel silicas and hydrocolloids, such as, e.g. carboxymethylcellulose, hydroxyethylcellulose, hydroxypropyl guar, hydroxyethyl starch, polyvinylpyrrolidone, high-molecular-weight polyethylene glycol, plant gums such as tragacanth, agar-agar, carrageen moss, gum arabic, xantham gum and carboxyvinylpolymers (e.g. Carbopol® types) are suitable. In addition to the mixtures of menthofuran and menthol compounds, the oral and dental care compositions can in particular surface-active substances, preferably anionic and nonionic high-foam surfactants, such as the abovementioned substances, but in particular alkylether sulphate salts, alkyl polyglucosides and mixtures thereof.

Further customary toothpaste additives are:

preservatives and antimicrobial substances such as, e.g. methyl, ethyl or propyl p-hydroxybenzoates, sodium sorbate, sodium benzoate, bromochlorophene, phenyl salicylate, thymol and the like;

antitartar active ingredients, e.g. organophosphates such as 1 hydroxyethane-1, 1 diphosphonic acid, 1 phosphonpropane-1,2,3 tricarboxylic acid and others, which are known, e.g. from U.S. Pat. No. 3,488,419, DE 2224430 A1 and DE 2343196 A1;

other anticaries substances such as, e.g., sodium fluoride, sodium monofluorophosphate, tin fluoride;

sweetening agents, such as, e.g. saccharin sodium, sodium cyclamate, sucrose, lactose, maltose, fructose or Apartam®, (L aspartyl L phenylalanine methyl ester), stevia extracts or the sweetening components thereof, in particular rebeaudiosides;

additional flavorings such as, e.g. eucalyptus oil, aniseed oil, fennel oil, cumin oil, methyl acetate, cinnamaldehyde, anethol, vanillin, thymol and also mixtures of these and other natural and synthetic flavourings;

pigments such as, e.g., titanium dioxide;

colorings;

buffer substances such as, e.g. primary, secondary or tertiary alkali metal phosphates or citric acid/sodium citrate;

wound-healing and anti-inflammatory substances such as, e.g. allantoin, urea, azulene, chamomile active ingredients and acetylsalicylic acid derivatives.

A preferred embodiment of the oral preparations are toothpastes in the form of an aqueous, pasty dispersion, containing polishing agents, moisture-retention agents, viscosity regulators and optionally contain further customary components, and also the mixture of menthofuran and menthol compounds in amounts of 0.5 to 2% by weight.

In mouthwashes, a combination with aqueous-alcoholic solutions of various concentration gradients of essential oils, emulsifiers, astringent and toning drug extracts, tartar-inhibiting, antibacterial additives and flavour correctors is easily possible. A further preferred embodiment of the invention is a mouthwash in the form of an aqueous or aqueous-alcoholic solution containing the mixture of menthofuran and menthol compounds in amounts of 0.5 to 2% by weight. In mouthwashes which are diluted before application, adequate effects can be achieved with higher concentrations corresponding to the intended dilution ratio.

To improve the flow behaviour, in addition, hydrotropic agents, such as, for example, ethanol, isopropyl alcohol or polyols can be used; these substances correspond substantially to the carriers described at the outset. Polyols which come into consideration here preferably have 2 to 15 carbon atoms and at least two hydroxyl groups. The polyols can contain even further functional groups, in particular amino groups, or be modified by nitrogen. Typical examples are glycerol;

alkylene glycols, such as, for example, ethylene glycol, diethylene glycol, propylene glycol, butylene glycol, hexylene glycol and also polyethylene glycols having an average molecular weight from 100 to 1000 daltons;

technical oligoglycerol mixtures having a degree of self-condensation of 1.5 to 10 such as technical diglycerol mixtures having a diglycerol content of 40 to 50% by weight;

methylol compounds such as, in particular, trimethylol ethane, trimethylol propane, trimethylol butane, pentaerythritol and dipentaerythritol;

low-alkyl glucosides, in particular those having 1 to 8 carbon atoms in the alkyl radical, such as, for example, methyl and butyl glucoside;

sugar alcohols having 5 to 12 carbon atoms, such as, for example, sorbitol or mannitol, sugars having 5 to 12 carbon atoms, such as, for example, glucose or sucrose;

amino sugars, such as, for example, glucamine;

dialcoholamines, such as diethanolamine or 2-amino-1,3-propanediol.

Suitable preservatives are, for example, phenoxyethanol, formaldehyde solution, parabens, pentanediol or sorbic acid, and also the silver complexes known under the name Surfacine® and the further classes of substances listed in annex 6, part A and B of the cosmetics directive.

Perfume oils which may be mentioned are mixtures of natural and synthetic odour substances. Natural odour substances are extracts of blossoms (lily, lavender, roses, jasmine, neroli, ylang-ylang), stalks and leaves (geranium, patchouli, petitgrain), fruits (aniseed, coriander, cumin, juniper), fruit skins (bergamot, lemon, oranges), roots (mace, angelica, celeriac, cardamom, costus, iris, calmus), woods (pine, sandal, guaiac, cedar, rosewood), herbs and grasses (tarragon, lemon grass, sage, thyme), needles and twigs (spruce, fir, pine, mountain pine), resins and balsams (galbanum, elemi, benzoin, myrrh, olibanum, opoponax). In addition, animal raw materials come into consideration, such as, for example, civet and castoreum. Typical synthetic odour substance compounds are products of the type of esters, ethers, aldehydes, ketones, alcohols and hydrocarbons. Odour substance compounds of the ester type are, e.g. benzyl acetate, phenoxyethyl isobutyrate, p tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexylpropionate, styrallyl propionate and benzyl salicylate. The ethers include, for example, benzyl ethyl ether, the aldehydes include, e.g. the linear alkanals having 8 to 18 carbon atoms, citral, citronellal, citronellyloxyacetaldehyde, cyclamen aldehyde, hydroxycitronellal, lilial and bourgeonal, the ketones include, e.g., the ionones, α isomethylionone and methyl cedryl ketone, the alcohols include anethole, citronellol, eugenol, isoeugenol, geraniol, linalool, phenylethyl alcohol and terpineol, the hydrocarbons include chiefly the terpenes and balsams. However, preference is given to using mixtures of various odour substances which together generate a corresponding fragrance note. Also essential oils of lower volatility which are generally used as aroma components are suitable as perfume oils, e.g. salvia oil, chamomile oil, clove oil, melissa oil, mint oil, cinnamon leaf oil, linden blossom oil, juniper berry oil, vetiver oil, olibanum oil, galbanum oil, labolanum oil and lavender oil. Preferably, bergamot oil, dihydromyrcenol, lilial, lyral, citronellol, phenylethyl alcohol, a hexylcinnamaldehyde, geraniol, benzylacetone, cyclamen aldehyde, linalool, boisambrene forte, Ambroxan, indole, hedione, sandelice, lemon oil, mandarin oil, orange oil, allyl amyl glycolate, cyclovertal, lavender oil, Salvia sclarea oil, β damascone, geranium bourbon oil, cyclohexyl salicylate, Vertofix Coeur, Iso-E-Super, Fixolide NP, evernyl, iraldein gamma, phenylacetic acid, geranyl acetate, benzyl acetate, rose oxide, romilllate, irotyl and floramate are used alone or in mixtures.

As flavourings, for example, peppermint oil, spearmint oil, aniseed oil, star anise oil, cumin oil, eucalyptus oil, fennel oil, lemon oil, wintergreen oil, clove oil, menthol and the like come into consideration.

Method and Use

The invention further relates to a method for enhancing the cooling effect caused by a preparation on oral administration, wherein a coolant mixture according to the invention described above is added to the preparation, preferably in amounts of about 0.005 to about 5% by weight, preferably of about 0.05 to about 1% by weight and especially of about 0.01 to about 0.5% by weight.

The invention finally relates to the use of mixtures as claimed in claim 1 as coolants, and in turn specifically is added preferably in amounts of about 0.005 to about 5% by weight, preferably of about 0.05 to about 1% by weight and especially of about 0.01 to about 0.5% by weight.

If the method and use are affected as elucidated above, the same quantities and preferred embodiments as described in detail above apply without this requiring repetition.

EXAMPLES

Performance Investigations

Examples 1 to 6, Comparative Examples C1 to C4

The cooling effect and flavor profile of various coolant mixtures were evaluated by a panel consisting of 5 trained testers. For this purpose, the mixtures were incorporated into an unsweetened and non-aromatized standard chewy candy preparation. The results are reported in table 1. The evaluation was reported according to the notation (5)=very true to (0)=largely not true. Data are mean values. Examples 1 to 6 are inventive while examples C1 to C4 serve as comparison.

TABLE 1

Sensory evaluation of coolant mixtures

| Components | C1 | C2 | C3 | C4 | 1 | 2 | 3 | 4 | 5 | 6 |
|---|---|---|---|---|---|---|---|---|---|---|
| Isobutyraldehyde | 100 | — | — | — | 99 | 99 | — | — | 45 | 0.5 |
| Isovaleraldehyde | — | 100 | — | — | — | — | 99 | 99 | 45 | — |
| Isobutyric acid | — | — | 100 | — | 1 | — | 1 | — | 5 | 0.5 |
| Isovaleric acid | — | — | — | 100 | — | 1 | — | 1 | 5 | — |
| Menthol | — | — | — | — | — | — | — | — | — | 10 |
| Menthyl acetate | — | — | — | — | — | — | — | — | — | 89 |
| Sensory evaluation | | | | | | | | | | |
| Cooling effect is strong | 3.2 | 3.1 | 3.0 | 3.1 | 4.2 | 4.4 | 4.1 | 4.4 | 4.6 | 4.9 |
| Cooling effect occurs rapidly | 2.1 | 2.0 | 2.2 | 2.5 | 3.8 | 3.5 | 3.7 | 3.6 | 4.1 | 4.4 |
| Stinging taste | 4.0 | 4.0 | 4.0 | 4.0 | 2.3 | 2.5 | 2.9 | 2.8 | 2.0 | 3.0 |
| Pungent taste | 4.0 | 4.0 | 3.9 | 3.8 | 2.5 | 2.1 | 2.1 | 2.4 | 2.3 | 2.8 |
| Bitter taste | 2.0 | 2.0 | 2.0 | 1.8 | 2.1 | 2.1 | 2.0 | 2.0 | 1.8 | 2.0 |

The examples and comparative examples show that the mixtures according to the invention exert a greater and more rapid cooling effect and are assessed sensorially as significantly greater than the individual substances.

A series of formulation examples are given below.

Example 1

Toothpaste (figures as % by weight)

| COMPONENTS | AMOUNT |
|---|---|
| Water (deionized) | to 100 |
| Sorbitol 70% | 45.00 |
| Trisodium phosphate | 0.10 |
| Saccharin | 0.20 |
| Sodium monofluorophosphate | 1.14 |
| PEG 1500 | 5.00 |
| Sident 9 (abrasive silica) | 10.00 |
| Sident 22 S (Thickening silica) | 8.00 |
| Sodium carboxymethylcellulose | 1.10 |
| Titanium (IV) oxide | 0.50 |
| Water (deionized) | 4.50 |
| Sodium lauryl sulfate (SLS) | 1.50 |
| Aroma mixture | 1.00 |
| Solbrol M (Sodium salt) (Methylparaben) | 0.15 |
| Coolant mixture I | 0.40 |

Example 2

Toothpaste with zinc citrate (figures as % by weight)

| COMPONENTS | AMOUNT |
|---|---|
| Water (deionized) | to 100 |
| Sorbitol 70% | 45.00 |
| Trisodium phosphate | 0.10 |
| Saccharin | 0.20 |
| Sodium monofluorophosphate | 1.14 |
| PEG 1500 | 5.00 |
| Sident 9 (abrasive silica) | 10.00 |
| Sident 22 S (Thickening silica) | 8.00 |
| Sodium carboxymethylcellulose | 1.10 |
| Zinc citrate | 1.00 |
| Titanium (IV) oxide | 0.50 |
| Water (deionized) | 4.50 |
| Sodium lauryl sulfate (SLS) | 1.50 |
| Aroma mixture | 1.00 |
| SymDiol ® 68 (1.2-Hexanediol. Caprylyl glycol) | 0.25 |
| Coolant mixture II | 0.10 |

Example 3

Mouthwash (figures as % by weight)

| COMPONENTS | AMOUNT |
|---|---|
| Ethyl alcohol | 10.00 |
| Cremophor CO 40 (PEG 40 hydrogenated castor oil) | 1.00 |
| Aroma mixture | 0.25 |
| Water (deionized) | To 100.00 |
| Sorbitol 70% | 5.00 |
| Sodium saccharin 450 | 0.07 |
| Sodium fluoride | 0.18 |
| Benzoic acid | 0.12 |
| Coolant mixture III | 0.30 |

Example 4

Dental gel (figures as % by weight)

| COMPONENTS | AMOUNT |
|---|---|
| Na carboxymethylcellulose | 0.40 |
| Sorbitol 70%. in water | 72.00 |
| Polyethylene glycol (PEG) 1500 | 3.00 |
| Na saccarinate | 0.07 |
| Na fluoride | 0.24 |
| Aroma mixture | 1.00 |
| Abrasive silica | 11.00 |
| Thickening silica | 6.00 |
| Sodium dodecyl sulfate (SDS) | 1.40 |
| Dist. water | to 100 |
| p-Hydroxybenzoic acid (PHB) ethyl ester | 0.15 |
| Coolant mixture IV | 0.20 |

Example 5

Anti-plaque toothpaste (figures as % by weight)

| COMPONENTS | AMOUNT |
|---|---|
| Carrageenan | 0.90 |
| Glycerol | 15.00 |
| Sorbitol 70%. in water | 25.00 |
| PEG 1000 | 3.00 |
| Na fluoride | 0.24 |
| Tetrapotassium diphosphate | 4.50 |
| Tetrasodium diphosphate | 1.50 |

-continued

Anti-plaque toothpaste (figures as % by weight)

| COMPONENTS | AMOUNT |
| --- | --- |
| Na saccarinate | 0.40 |
| Precipitated silica | 20.00 |
| Titanium dioxide | 1.00 |
| Triclosan | 0.30 |
| Spearmint flavor (comprising 60 wt. % I-carvone and 25 wt. % I-menthol) | 1.00 |
| Sodium dodecyl sulfate | 1.30 |
| Dist. water | to 100 |
| Benzylalcohol | 0.50 |
| Coolant mixture V | 0.25 |

Example 6

Toothpaste for sensitive teeth (figures as % by weight)

| COMPONENTS | AMOUNT |
| --- | --- |
| Na carboxymethylcellulose | 0.70 |
| Xanthan gum | 0.50 |
| Glycerol | 15.00 |
| Sorbitol 70%. in water | 12.00 |
| Potassium nitrate | 5.00 |
| Sodium monofluorophosphate | 0.80 |
| Na saccharinate | 0.20 |
| Aroma mixture | 1.00 |
| Ca carbonate | 35.00 |
| Silicon dioxide | 1.00 |
| Sodium dodecyl sulfate (SDS) | 1.50 |
| Dist. water | to 100 |
| PHB methyl ester and PHB propyl ester | 0.20 |
| Coolant mixture I | 0.50 |

Example 7

Toothpaste and mouthwash 2:1 (figures as % by weight)

| COMPONENTS | AMOUNT |
| --- | --- |
| Sorbitol | 40.00 |
| Glycerol | 20.00 |
| Ethanol | 5.00 |
| Water | to 100 |
| Na monofluorophosphate | 0.75 |
| Saccharin | 0.20 |
| Sident 9 (abrasive silicon dioxide) | 20.00 |
| Sident 22 S (thickening silicon dioxide) | 2.00 |
| Sodium carboxymethylcellulose | 0.30 |
| Sodium lauryl sulfate (SDS) | 1.20 |
| Color (Suspension. 1% in water) C.I. Pigment Blue 15 | 0.50 |
| Aroma mixture | 0.90 |
| Solbrol M. sodium salt (methylparaben. sodium salt) | 0.20 |
| Coolant mixture II | 0.30 |

Example 8

Mouthwash with fluoride (figures as % by weight)

| COMPONENTS | AMOUNT |
| --- | --- |
| Ethanol | 7.00 |
| Glycerol | 12.00 |

-continued

Mouthwash with fluoride (figures as % by weight)

| COMPONENTS | AMOUNT |
| --- | --- |
| Na fluoride | 0.05 |
| Pluronic F-127 ® (BASF. surface-active substance) | 1.40 |
| Na phosphate buffer pH 7.0 | 1.10 |
| Na saccharinate | 0.10 |
| Aroma mixture | 0.15 |
| Chlorhexidine digluconate | 0.2 |
| Dist. water | to 100 |
| Sorbic acid | 0.20 |
| Coolant mixture III | 0.30 |

Example 9

Sugar-free chewing gum (figures as % by weight)

| COMPONENTS | AMOUNT |
| --- | --- |
| Chewing gum base | 30.00 |
| Sorbitol. powder | to 100 |
| Palatinite | 9.50 |
| Xylitol | 2.00 |
| Mannitol | 3.00 |
| Aspartame | 0.10 |
| Acesulfame K | 0.10 |
| Emulgum/emulsifier | 0.30 |
| Sorbitol 70%. in water | 14.00 |
| Glycerol | 1.00 |
| Aroma mixture | 1.50 |
| Coolant mixture IV | 0.20 |

The invention claimed is:

1. A coolant mixture comprising:
(a) at least one compound of the formula (I)

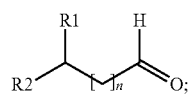

(b) at least one compound of the formula (II)

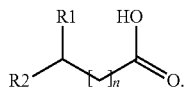

wherein $R^1$ is in each case hydrogen or a methyl group, $R^2$ is in each case a methyl, ethyl or propyl group and n is 0, 1 or 2; and (c) optionally a further coolant wherein said mixture comprises:
(a) about 90 to about 99% by weight substances of the formula (I),
(b) about 1 to about 10% by weight substances of the formula (II), and
(c) 0 to about 90% by weight further coolants with the proviso that the components add up to 100% by weight.

2. The coolant mixture, according to claim 1, wherein, said mixture comprises isobutyraldehyde or isovaleraldehyde or mixtures thereof as component (a).

3. The coolant mixture, according to claim 1, wherein said mixture comprises isobutyric acid or isovaleric acid or mixtures thereof as component (b).

4. The coolant mixture, according to claim 1, wherein said mixture comprises one selected from menthol, menthyl acetate, and mixtures thereof as component (c).

5. The coolant mixture, according to claim 1 said mixture comprises at least one mixture of components (a) and (b) selected from:
   (i) isobutyraldehyde and isobutyric acid;
   (ii) isovaleraldehyde and isovaleric acid;
   (iii) isobutyraldehyde and isovaleric acid;
   (iv) isovaleraldehyde and isobutyric acid; and
   (v) isobutyraldehyde, isobutyric acid, isovaleraldehyde and isovaleric acid.

6. A preparation for oral administration comprising the coolant mixture, according to claim 1.

7. The preparation, according to claim 6, wherein said preparation takes a form of one selected from foodstuffs, pharmaceutical preparations, mouth compositions, dental care compositions, and combinations thereof.

8. The preparation, according to claim 7, wherein said preparation takes a form of one selected from hard candies, chewy candies, and chewing gums.

9. The preparation, according to claim 7, wherein said preparation takes a form of a cold remedy.

10. The preparation, according to claim 7, wherein said preparation takes a form of one selected from toothpastes, mouthwashes, and medicinal chewing gums.

11. The preparation, according to claim 6, wherein said preparation comprises the coolant mixture in an amount of from about 0.005 to about 5% by weight-based on the finished preparation.

12. A method for enhancing the cooling effect caused by a preparation on oral administration, the method comprising adding the coolant mixture, according to claim 1, to the preparation.

13. The preparation according to claim 9, wherein the cold remedy is one selected from syrups, sprays, and candies.

* * * * *